(12) United States Patent
Trudsoe

(10) Patent No.: US 8,716,176 B2
(45) Date of Patent: May 6, 2014

(54) LOW SOLUBLE SOLIDS ACID GELS AND METHODS FOR MAKING SAME

(75) Inventor: Jens Eskil Trudsoe, Roskilde (DK)

(73) Assignee: CP Kelco ApS, Lille Skensved (DK)

( * ) Notice: Subject to any disclaimer, the term of this patent is extended or adjusted under 35 U.S.C. 154(b) by 123 days.

(21) Appl. No.: 13/585,493

(22) Filed: Aug. 14, 2012

(65) Prior Publication Data

US 2013/0072381 A1  Mar. 21, 2013

Related U.S. Application Data

(60) Provisional application No. 61/536,231, filed on Sep. 19, 2011.

(51) Int. Cl.
*B01J 20/24* (2006.01)

(52) U.S. Cl.
USPC .......................... 502/404; 502/439; 502/526

(58) Field of Classification Search
USPC .................................. 502/404, 401, 439, 526
See application file for complete search history.

(56) References Cited

U.S. PATENT DOCUMENTS

| | | | |
|---|---|---|---|
| 4,294,821 A | 10/1981 | Neumiller | |
| 4,447,243 A | 5/1984 | Claiborne | |
| 5,534,249 A | 7/1996 | Maurer | |
| 5,541,234 A | 7/1996 | Unger et al. | |
| 5,603,928 A | 2/1997 | Noda | |
| 5,626,901 A | 5/1997 | Pedersen | |
| 5,641,533 A | 6/1997 | Pedersen | |
| 5,741,482 A | 4/1998 | Modi | |
| 5,817,300 A | 10/1998 | Cook et al. | |
| 5,879,622 A | 3/1999 | Meehan | |
| 5,968,498 A | 10/1999 | Okada et al. | |
| 6,631,722 B2 | 10/2003 | MacAdam et al. | |
| 7,229,612 B2 | 6/2007 | Levi et al. | |
| 7,434,586 B2 | 10/2008 | Higashi et al. | |
| 7,741,261 B1 | 6/2010 | Guerrero | |
| 2002/0142992 A1 | 10/2002 | Scherr | |
| 2005/0037080 A1 | 2/2005 | Lynch et al. | |
| 2006/0127991 A1 | 6/2006 | Christensen et al. | |
| 2012/0251484 A1 | 10/2012 | Trudsoe et al. | |

FOREIGN PATENT DOCUMENTS

| | | |
|---|---|---|
| JP | 2003070893 | 3/2003 |
| JP | 2005287570 | 10/2005 |

OTHER PUBLICATIONS

International Search Report for PCT/EP2012/067428, mailed Nov. 27, 2012.
Written Opinion of the International Search Authority for PCT/EP2012/067428, mailed Nov. 27, 2012.
http://www.vinegarbook.net/vinegar_book_odors_page_1.shtml.
http://www.ehow.com/how_4481971_clean-remove-odor-vinegar.html.
http://www.cpkelco.com/market_food/app-fruit.html.

*Primary Examiner* — Edward Johnson
(74) *Attorney, Agent, or Firm* — Sutherland Asbill & Brennan LLP

(57) ABSTRACT

A gel composition including a low ester pectin in an amount from about 1.0 to about 2.5 percent by weight of the gel composition, acetic acid in an amount such that the gel composition has a pH from about 2.4 to about 3.5, and having a gel strength from about 5 grains to about 250 grams. A method for making the gel is also disclosed. The method includes dissolving a low ester pectin in an acetic acid solution, heating the mixture to a temperature from about 80° C. to about 100° C., and cooling the mixture.

20 Claims, No Drawings

LOW SOLUBLE SOLIDS ACID GELS AND METHODS FOR MAKING SAME

RELATED APPLICATIONS

This application claims priority under 35 U.S.C. §119(e) to U.S. Provisional Application 61/536,231 filed on Sep. 19, 2011, the disclosure of which is expressly incorporated by reference in its entirety.

TECHNICAL FIELD

The invention relates to the field of gels and more particularly relates to low soluble solids acid gels having improved odor absorption properties.

BACKGROUND

Gels are used in many applications including cleaning products, such as for surfaces, fabrics, and the like, and air treatment materials for continuous release of volatile air treatment components such as perfumes, disinfectants, bactericides, insecticides, and the like. Typical air freshener gels and gel-based cleaning products incorporate perfumes and other fragrance products to overpower malodors.

Air freshener compositions that absorb malodors have been developed. For example, an alcoholic solution of menthol and lemon oil is known to neutralize offensive odors. Zirconium compounds have been used to reduce odor from primary, secondary and tertiary amines or ammonia. Dialkali monometal organic ligand chelate has been used as an oxidation catalyst in the presence of oxygen to neutralize odor-causing materials. A composition containing diethylene glycol, propylene glycol, triethylene glycol, glycerin, diethanolamide and an unsaturated fatty acid has been used to absorb odor.

Vinegar is also known to absorb odors and is commonly used in liquid solutions for cleaning and deodorizing. Seaweed-based gels and gel/semi-gel food products have incorporated vinegar in low concentrations to lower pH and/or increase the rate of gelatin.

It would be desirable to incorporate odor-absorbing compositions into air freshening gels and gel-based cleaning products to produce gel-based products that absorb malodor as opposed to masking or overpowering malodors.

SUMMARY OF THE INVENTION

An odor absorbing gel composition is provided. The gel composition includes a low ester pectin in an amount from about 1.0 to about 3.5 percent by weight of the gel composition and acetic acid in an amount such that the gel composition has a pH from about 2.4 to about 3.5, and has a gel strength from about 5 grams to about 250 grams.

A method of making an odor absorbing gel composition is also provided. The method includes: (i) dissolving a low ester pectin in an acetic acid solution to form an acidic pectin mixture; (ii) heating the acidic pectin mixture to a temperature from about 80° C. to about 100° C.; and (iii) cooling the mixture to room temperature to form a gel composition wherein the low ester pectin is present in the gel composition in an amount from about 1.0 to about 3.5 percent by weight of the gel composition, the acetic acid is present in the gel composition in an amount such that the gel composition has a pH from about 2.4 to about 3.5, and the gel composition has a gel strength from about 5 grams to about 250 grams.

Embodiments of this invention are set forth below in the following detailed description and claims.

DETAILED DESCRIPTION OF THE INVENTION

The invention addresses the above-described need by providing low soluble solids acid gels having potential uses including odor absorption (e.g., in rooms, in refrigerators, and in air conditioning systems) and cleaning (e.g., toilet flush, textile rinse). This invention encompasses gel compositions and methods of making gel compositions.

Several embodiments of the invention are described below including an odor absorbing gel composition, although the embodiments of this invention may also be used for other applications. Parameters of different steps, components, and products of embodiments are described separately, but may be combined consistently with this description and claims to enable still other embodiments as will be understood by those skilled in the art. Throughout the specification, examples, and claims, unless otherwise indicated, percents refer to percent by weight.

In one aspect, an odor absorbing gel composition is provided. The gel composition includes a low ester pectin in an amount from about 1.0 to about 15 percent by weight of the gel composition and acetic acid in an amount such that the gel composition has a pH from about 2.4 to about 3.5, and has a gel strength from about 5 grams to about 250 grams.

The gel compositions include a low ester pectin which serves as a gelling agent. For example, the gel composition may contain a conventional low ester pectin or an amidated low ester pectin.

In some embodiments, the tow ester pectin is a conventional (i.e., non-amidated) low ester pectin. Acid gels made with conventional low ester pectins are characterized as gummy and dry. Conventional low ester pectin gels also display high solubility.

According to some embodiments, the conventional low ester pectin may have a degree of esterification (DE) of less than about 55, from about 15 to 55, from about 25 to 45, or from about 30 to about 40. As the DE value increases, the solubility of the conventional low ester pectin in the gel composition improves. For example, at a DE value below about 15, the conventional low ester pectin is poorly soluble in the composition. However, a conventional low ester pectin having a DE value above about 55 will result in a weak, soft acid gel.

According to some embodiments, the conventional low ester pectin may be present in an amount from about 1.0 to about 3.5 percent by weight of the gel composition, or from about 1.5 to about 3.5 percent by weight of the composition. At a higher pectin concentration, the resulting gels thicken faster, but may display lumps.

In some embodiments, the low ester pectin is an amidated low ester pectin. Acid gels made with amidated low ester pectins are characterized as firm and brittle.

According to some embodiments, the amidated low ester pectin may have a degree of amidation (DA) from about 15 to about 30. The solubility of the amidated low ester pectin in the compositions generally increases with decreasing DA value. For example, at a DA value above about 30, amidated low ester pectin not dissolve completely.

In some embodiments, the amidated low ester pectin may be present in an amount from about 1.0 to about 3.5 percent by weight of the gel composition or from about 1.5 to about 3.5 percent by weight of the gel composition.

The gel compositions also include acetic acid which serves as an odor absorbing and pH reducing agent. The acetic acid may include vinegar, glacial acetic acid, or a combination thereof. The vinegar may be of household quality. In some embodiments, other acids may also be used. For example, citric acid, lactic acid, malic acid, tartaric acid, and other organic acids may be used in the pH ranges disclosed herein.

In certain embodiments, the acetic acid includes a combination of vinegar and glacial acetic acid having a weight ratio of glacial acetic acid to vinegar of less than about 0.35, less than about 0.15, less than about 0.10 or from about 0.03 to about 0.35. For example, a gel composition may include a conventional low ester pectin and a combination of vinegar and glacial acetic acid having a weight ratio of glacial acetic acid to vinegar less than about 0.15.

In some embodiments, the gel compositions containing conventional low ester pectins include acetic acid in an amount to such that the gel composition has a pH from about 2.4 to about 3.5 or from about 2.45 to about 3.25. Conventional low ester pectin gels are thicker at high pH and thinner at low pH.

In some embodiments, the gel compositions containing amidated low ester pectins include acetic acid in an amount to such that the gel composition has a pH from about 2.95 to about 3.45. The solubility of amidated low ester pectin in composition is reduced when the pH is reduced with glacial acetic acid and the pH of amidated low ester pectin gel compositions should not be reduced below about 2.95. However, a lower pH results in a brittle gel having a high melting temperature.

Additives may optionally be included in the gel compositions described above. For example, calcium acetate, calcium chloride, and other soluble calcium salts may be added to improve the gelling of the composition. For example, compositions containing convention low ester pectins display increased get and break strengths with increased amounts of calcium acetate. The gelling effect of the calcium acetate increases with decreasing pH.

In certain embodiments, the gel composition includes calcium acetate in an amount from about 0.0160 to about 0.0220 percent by weight of the gel composition.

The gel compositions described herein are desirably dry, with low to substantially no syneresis (i.e., exudation of liquid from the gel), and strong, with high gel and break strengths.

In certain embodiments, low ester pectin gels containing as little as 1.5% pectin are dry. Decreasing the pectin concentration below 1.5% may result in a very thin gel.

In some embodiments, the gel compositions containing conventional low ester pectins have gel strengths from about 5 grams to about 250 grams, from about 5 grams to about 150 grams, from about 5 grams to about 100 grams, or from about 5 grams to about 40 grams. The strength of gels made with conventional low ester pectins increases with increasing pectin concentration. Furthermore, gels made with conventional low ester pectins having a lower DE value display higher gel and break strengths than gels made with conventional low ester pectins having a higher DE value. The break strength of conventional low ester pectin gels is sensitive to pH, and increases with decreasing pH.

In some embodiments, the gel compositions containing amidated low ester pectins have gel strengths from about 5 grams to about 250 grams, from about 30 grams to about 250 grams, from about 50 grams to about 250 grams, from about 100 grams to about 250 grams, or from about 150 grams to about 250 grams. Without the addition of glacial acetic acid, the concentration of amidated low ester pectin must be at least around 2 percent by weight of the composition to avoid syneresis. When glacial acetic acid is included in the composition, the concentration of amidated low ester pectin must be at least about 3 percent by weight of the composition to avoid syneresis.

In one embodiment, a gel composition includes a conventional low ester pectin having a degree of esterification from about 30 to about 40 and present in an amount from about 1.5 to about 3.5 percent by weight of the gel composition, and calcium acetate in an amount from about 0.0160 to about 0.0220 percent by weight of the gel composition.

In another embodiment, a gel composition includes vinegar and an amidated low ester pectin having a DA from about 15 to about 30 in an amount from about 2.0 to about 3.5 percent by weight of the gel composition.

In another embodiment, a gel composition includes a combination of vinegar and glacial acetic acid having a weight ratio of glacial acetic acid to vinegar of from about 0.025 to about 0.05 and an amidated low ester pectin having a DA from about 15 to about 30 and present in an amount from about 3.0 to about 3.5 percent by weight of the gel composition.

In another aspect, a method of making an odor absorbing gel composition is provided. The method includes the steps of: (i) dissolving a low ester pectin in an acetic acid solution to form an acidic pectin mixture; (ii) heating the acidic pectin mixture to a temperature from about 80° C. to about 100° C.; and (iii) cooling the mixture to room temperature to form a gel. The low ester pectin is present in the gel composition in an amount from about 1.0 to about 3.5 percent by weight of the get composition, the acetic acid is present in the gel composition in an amount such that the gel composition has a pH from about 2.4 to about 3.5, and the gel composition has a gel strength from about 5 grams to about 250 grams.

Gel compositions made in accordance with embodiments of this invention are useful for odor-absorbing applications such as air freshening gels and gel-based cleaning products because they absorb malodor. Such gel compositions may be used in many applications suitable for odor removal including but not limited to refrigerators, kitchens, pantries, bathrooms, automobiles, and the like. According to certain embodiments, gel compositions made in accordance with embodiments of this invention can be disposed in a housing that allows air to contact the gel composition for removal of odor from the air. In certain embodiments, the housing may selectively allow air to contact the gel composition for removal of odor from the air and, alternatively, limit access of air to the gel or enclose the gel composition and create a barrier to air outside the housing.

The components may be combined in amounts that provide the gel compositions described above.

The methods and compositions described herein will be further understood with reference to the following non-limiting examples and the accompanying tables, in which several embodiments of the application are described.

EXAMPLES

Low soluble solids acid gels were made using conventional low ester pectins and amidated low ester pectins. Household vinegar having a pH of about 2.59, analytical grade glacial acetic acid, demineralized water, and analytical grade calcium acetate were also utilized. Conventional low ester pectins of DE 21, 31, 38, and 51 were produced according to the method described in U.S. Patent Application Publication No. 2006/0127991, which is incorporated herein by reference in its entirety. Amidated low ester pectins of DA 18, 24, and 31 were obtained.

Gels were made according to the composition set forth in Table 1 and the following method.

TABLE 1

| Composition of gels | |
|---|---|
| Ingredients | Mass (g) |
| Vinegar | 200 − x |
| Pectin | 6.6 |
| Glacial acetic acid | x |
| CaAc | y |
| Net mass adjusted | 220 |

The pectin was dispersed in an acetic acid solution containing vinegar and, optionally, glacial acetic acid, while stirring. The solution was heated to 90° C. and stirred to full dispersion. The solution was poured into a crystallizing dish having a diameter of about 40 mm, a height of about 45 mm, and an adhesive tape barrier to allow filling above the rim. The solutions was cooled overnight at room temperature.

The resulting gels were measured at room temperature on a TA.XTPlus Texture Analyzer produced by Stable Micro Systems, with a 6 ram plunger, 0.5 mm/sec speed, and 24 mm distance setting. Gel strength was defined as the load to depress the gel by 2.5 mm. The pH of the resulting gels were measured. Gelling and melting temperatures of the resulting gels were measured on a Haake RheoStress RS100 Rheometer equipped with cup Z20/48 mm and rotor Z20 DIN produced by Thermo Electron GmbH, Germany. The data collected from these tests is shown below for gels produced using both amidated low ester pectins (LMA) and conventional low ester pectins (LMC).

Acid Gels Produced Using Conventional Low Ester Pectins (LMC)

Tables 2-11 show the data on gels made with conventional low ester pectins (LMC) at varying DE, pectin concentration, glacial acetic acid volume, and calcium acetate amount. The pH, break strength, gel strength, gelling temperature, melting temperature, dispersion and gel characteristics are shown for each sample. The conventional low ester pectins used in these samples correspond to the GENU Explorer low ester pectins produced by CP Kelco.

Table 2 compares two gel composition samples made using DE 21 LMC and varying volumes of glacial acetic acid.

TABLE 2

| Gels with LMC—DE = 21. Effect of glacial acetic acid | | | | | | | | |
|---|---|---|---|---|---|---|---|---|
| Sample | Glacial (ml) | pH | BS (g) | GS (g) | $T_G$ (° C.) | $T_M$ (° C.) | Disp. | Gel | Other comments |
| 20100715-1.2 | 0 | 2.81 | 40 | 7 | 81 | >90 | OK Thick after 15 sec | Weak Dry Gummy | Not dissolved Some air |
| 20100715-1.3 | 10 | 2.65 | 69 | 15 | >90 | >90 | OK Thick after 2-3 min | Weak Dry Gummy | Not dissolved Some air |

Table 3 compares get compositions made using DE 31 LMC and varying volumes of glacial acetic acid.

TABLE 3

| Gels with LMC—DE = 31. Effect of glacial acetic acid | | | | | | | | |
|---|---|---|---|---|---|---|---|---|
| Sample | Glacial (ml) | pH | BS (g) | GS (g) | $T_G$ (° C.) | $T_M$ (° C.) | Disp. | Gel | Other comments |
| 20100713-1.1 | 0 | 3.11 | 42 | 8 | 41 | 46 | Difficult Very thick Thins at about 50° C. | Weak Dry Gummy | Dissolved, air |
| 20100713-1.2 | 5 | 3.01 | 28 | 6 | 42 | 45 | Difficult Very thick. | Weak Dry Gummy | Dissolved, air |
| 20100713-1.3 | 10 | 2.93 | 21 | 5 | 42 | 46 | Less thick | Weak Dry Gummy | Dissolved, air |
| 20100714-1.1 | 15 | 2.82 | 37 | 7 | 48 | 51 | Less thick | Weak Dry Gummy | Dissolved, air |
| 20100714-1.2 | 20 | 2.76 | 53 | 7 | 52 | 56 | Less thick | Weak Dry Gummy | Dissolved, less air |
| 20100714-1.3 | 25 | 2.69 | 87 | 9 | 52 | 55 | Less thick Stays thin for longer | Weak Dry Gummy | Dissolved, less air |
| 20100715-1.1 | 35 | 2.56 | 126 | 15 | 61 | 68 | OK Thick after 1-2 min | Weak Dry Gummy | Dissolved, less air |

Table 4 compares get compositions made using DE 31 LMC and varying amounts of glacial acetic acid and calcium acetate.

TABLE 4

Gels with LMC—DE = 31. Effect of calcium acetate

| Sample | Glacial (ml) | CaAc (g) | pH | BS (g) | GS (g) | $T_G$ (° C.) | $T_M$ (° C.) | Disp. | Gel | Other comments |
|---|---|---|---|---|---|---|---|---|---|---|
| 20100909-1.1 | 0 | 0.00 | 3.11 | — | 9 | 41 | 46 | Very thick Lumps. | Weak Gummy Dry | Dissolved. Air |
| 20100909-1.3 | 0 | 0.09 | 3.17 | 90 | 13 | 43 | 48 | Thick with time Lumps | Gummy Dry | No air. Dissolved. |
| 20100909-1.4 | 0 | 0.17 | 3.22 | 181 | 21 | 51 | 68 | Slowly thick Lumps. | Gummy Dry | Air. Dissolved |
| 20100910-1.1 | 35 | 0.00 | 2.61 | 166 | 24 | 63 | 66 | OK | Gummy Dry | No air. Dissolved. |
| 20100910-1.2 | 35 | 0.04 | 2.62 | 184 | 37 | 80 | 90 | OK | Gummy Dry | No air. Dissolved. |
| 20100914-1.1 | 25 | 0.04 | 2.73 | 149 | 22 | 63 | 79 | OK Thick after 1-2 min | Gummy Dry | Dissolved, no air |

Table 5 compares gel compositions made using varying concentrations of DE 31 LMC, 25 ml of glacial acetic acid, and 0.04 g calcium acetate.

TABLE 5

Gels with LMC—DE = 31. Effect of pectin concentration

| Sample | Pectin % | Glacial (ml) | CaAc (g) | pH | BS (g) | GS (g) | $T_G$ (° C.) | $T_M$ (° C.) | Disp. | Gel |
|---|---|---|---|---|---|---|---|---|---|---|
| 20101115-1.1 | 2 | 25 | 0.04 | 2.61 | 59 | 10 | 58 | 66 | OK Thin No lumps | Soft Gummy Dry Dissolved |
| 20101115-1.2 | 1.5 | 25 | 0.04 | 2.54 | 50 | 9 | 57 | 64 | OK Thin No lumps | Soft Gummy Dry Dissolved |

Table 6 compares gel compositions made using DE 38 LMC and varying volumes of glacial acetic acid.

TABLE 6

Gels made with LMC—DE = 38. Effect of glacial acetic acid

| Sample | Glacial (ml) | pH | BS (g) | GS (g) | $T_G$ (° C.) | $T_M$ (° C.) | Disp. | Gel | Other comments |
|---|---|---|---|---|---|---|---|---|---|
| 20100719-1.1 | 0 | 3.24 | 0 | 4 | 31 | 35 | Difficult Thick Lumps | Very weak Gummy Dry | Dissolved, air |
| 20100719-1.2 | 10 | 3.01 | 0 | 4 | 33 | 37 | Difficult Very thick | Very weak Gummy Dry | Dissolved, air |
| 20100719-1.3 | 20 | 2.86 | 0 | 5 | 37 | 41 | Thick Fewer lumps | Very weak Gummy Dry | Dissolved |
| 20100914-1.2 | 35 | 2.66 | 61 | 9 | 46 | 51 | Thickens quickly Some lumps | Weak Gummy Dry | Dissolved, no air |

Table 7 compares gel compositions made using DE 38 LMC 35 ml glacial acetic acid, and varying amounts of calcium acetate.

TABLE 7

Gels made with LMC—DE = 38. Effect of calcium acetate

| Sample | Glacial (ml) | CaAc (g) | pH | BS (g) | GS (g) | $T_G$ (° C.) | $T_M$ (° C.) | Disp. | Gel | Other comments |
|---|---|---|---|---|---|---|---|---|---|---|
| 20100914-1.2 | 35 | 0 | 2.66 | 61 | 9 | 46 | 51 | Thickens quickly Some lumps | Weak Gummy Dry | Dissolved No air |
| 20100914-1.3 | 35 | 0.04 | 2.67 | 93 | 14 | 60 | 73 | Thickens quickly Some lumps | Weak Gummy Dry | Dissolved No air |
| 20100929-1.1 | 35 | 0.06 | 2.60 | 81 | 16 | 62 | 73 | Disp OK Thickens after 1 min | Weak Gummy Dry | Dissolved No air |

Table 8 compares gel compositions made using varying concentrations of DE 38 LMC, 35 ml glacial acetic acid, and 0.045 g calcium acetate.

TABLE 8

Gels made with LMC—DE = 38. Effect of pectin concentration

| Sample | Pectin % | Glacial (ml) | CaAc (g) | pH | BS (g) | GS (g) | $T_G$ (° C.) | $T_M$ (° C.) | Disp. | Gel | Other comments |
|---|---|---|---|---|---|---|---|---|---|---|---|
| 20101115-1.3 | 3 | 35 | 0.045 | 2.64 | 73 | 12 | 54 | 62 | Thick in 1-2 min Few lumps | Soft Gummy | Dry Dissolved |
| 20101116-1.1 | 2 | 35 | 0.045 | 2.53 | 41 | 7 | 56 | 64 | OK Thick in 5 min Few lumps | Soft Gummy | Dry Dissolved |
| 20101116-1.2 | 1.5 | 35 | 0.045 | 2.46 | 24 | 5 | 52 | 59 | OK Thin No lumps | Soft Gummy | Dry Dissolved |

Table 9 shows the effect of a change in the order of addition of ingredients during dispersing at room temperature. DE 38 LMC pectin was dispersed in the glacial acetic acid, then calcium acetate was added, and vinegar was stirred in.

TABLE 9

Gels made with LMC—DE = 38. Effect of change in order of addition.

| Sample | Pectin % | Glacial (ml) | CaAc (g) | pH | BS (g) | GS (g) | $T_G$ (° C.) | $T_M$ (° C.) | Disp. | Gel | Other comments |
|---|---|---|---|---|---|---|---|---|---|---|---|
| 20101116-1.3 | 2 | 35 | 0.045 | 2.54 | 43 | 1 | 53 | 61 | In glacial: Thin No lumps With CaAc: No change With vinegar: Fine disp No lumps Thickens in 5 min. | Soft Gummy | Dry Dissolved |

Table 10 compares gel compositions made using DE 51 LMC and varying volumes of glacial acetic acid.

TABLE 10

Gels made with LMC—DE = 51. Effect of glacial acetic acid.

| Sample | Glacial (ml) | pH | BS (g) | GS (g) | $T_G$ (° C.) | $T_M$ (° C.) | Disp. | Gel | Other comments |
|---|---|---|---|---|---|---|---|---|---|
| 20100721-1.1 | 0 | 3.16 | — | — | 23 | 27 | Difficult Thick Lumps | Too weak to measure | Dissolved, much air |
| 20100721-1.2 | 10 | 2.87 | — | — | 24 | 28 | Thick Lumps | Too weak to measure | Dissolved, much air |
| 20100721-1.3 | 20 | 2.73 | — | — | 26 | 30 | Thick Lumps | Too weak to measure | Dissolved, much air |
| 20100722-1.1 | 50 | 2.46 | — | — | 40 | 45 | Thick Lumps | Too weak to measure | Dissolved, no air |

Table 11 compares gel compositions made using DE 51 LMC, 50 ml glacial acetic acid and varying amounts of calcium acetate.

TABLE 11

Gels made with LMC—DE = 51. Effect of calcium acetate

| Sample | Glacial (ml) | CaAc (g) | pH | BS (g) | GS (g) | $T_G$ (° C.) | $T_M$ (° C.) | Disp. | Gel | Other comments |
|---|---|---|---|---|---|---|---|---|---|---|
| 20100929-1.3 | 50 | 0.07 | 2.45 | 37 | 7 | 49 | 60 | Disp OK Thickens in 1 min | Weak Gummy Dry | Dissolved No air |
| 20100929-1.2 | 50 | 0.17 | 2.47 | 35 | 14 | 90 | 90 | Disp OK Thick during heating Thick at filling | Weak Gummy Dry | No air |

The data on LMC compositions demonstrates that a DE of about 21 is too low because the pectin is poorly soluble. However, as the DE increases, the solubility is improved.

At a DE of about 31, as the pH is reduced, the gelling and melting temperatures of the gel composition are increased, but the melting temperature still remains below about 80° C. at pH about 2.5, which indicates perfect dissolution. Particularly, the break strength is sensitive to pH, and increases with decreasing pH.

Using LMC having DE of about 31, with increasing addition of glacial acetic acid, thus decreasing pH, both gelling temperature and melting temperature are increased as the amount of calcium acetate is increased. More calcium acetate can be added when less glacial acetic acid is used. The break strength of gels made with LMC having DE about 31 can be increased with calcium acetate. The lower the pH, the greater the effect of calcium acetate.

The strengths of gels made with conventional low ester pectin increase with increasing pectin concentration. Surprisingly, the gels made with as little as 1.5% pectin were still dry.

For compositions made with LMC having a DE of about 38, the effect of pH follows the same trend as for LMC with DE of about 31, but the gelling and melting temperatures are lower than for the lower DE compositions. Also, for compositions made with LMC having a DE of about 38, the break strength is particularly sensitive to pH, but both break and gel strengths are lower than for the lower DE compositions. The melting and gelling temperatures are lower than those for the compositions using LMC with a DE of about 31, and compositions using LMC with a DE of 38 can dissolve even in the presence of more than 0.05 g calcium acetate.

Compared to DE 31 LMC compositions, the DE 38 LMC compositions have a lower break strength and gel strength. As with the lower DE material, DE 38 LMC compositions are stronger as the pectin concentration increases. However, the strengths are lower than for the lower DE material. Again, even the lowest concentration of LMC pectin results in dry gels.

For compositions made using DE 51 LMC, the effect of pH on gelling and melting temperature follows the trend of lower DE materials, but the temperatures are even lower. However, the resulting gels were too weak to measure on the texturizer. Compositions using 51 DE LMC dissolve at much higher concentrations of calcium acetate than the lower DE compositions. The break strength is substantially unchanged with increasing content of calcium acetate, whereas the gel strength increases with increasing amounts of calcium acetate. However, the 51 DE LMC gels are considerably softer than the lower DE compositions.

These tests further demonstrate that if LMC pectin is dispersed in glacial acetic acid before adding calcium acetate and vinegar, lumping can be avoided.

Overall, compared to gels made with amidated tow ester pectin, the gels made with conventional low ester pectin are weaker, gummy and completely dry. These gels also display much better solubility.

Acid Gels Produced Using Amidated Low Ester Pectins (LMA)

Tables 12-16 show the data on gels made with amidated low ester pectins at varying DA, pectin concentration and glacial acetic acid volume. The pH, break strength, gel strength, gelling temperature, melting temperature, dispersion and gel characteristics are shown for each sample.

Table 12 compares two samples containing DA 31 LMA and varying volumes glacial acetic acid.

TABLE 12

Gels made with LMA—DA = 31. Effect of glacial acetic acid

| Sample | Glacial (ml) | pH | BS (g) | GS (g) | $T_G$ (° C.) | $T_M$ (° C.) | Disp. | Gel | Other comments |
|---|---|---|---|---|---|---|---|---|---|
| 20100705-1.1 | 0 | 3.31 | 1114 | 359 | 56 | 84 | OK | Firm | Not completely dissolved |
| 20100705-1.2 | 5 | 3.16 | 13 | 11 | >90 | >90 | OK | Very weak gel | Not dissolved |

Table 13 compares gels made with DA 24 LMA and varying volumes of glacial acetic acid.

TABLE 13

Gels made with LMA—DA = 24. Effect of glacial acetic acid.

| Sample | Glacial (ml) | pH | BS (g) | GS (g) | $T_G$ (° C.) | $T_M$ (° C.) | Disp. | Gel | Other comments |
|---|---|---|---|---|---|---|---|---|---|
| 20100705-1.3 | 0 | 3.44 | 1024 | 105 | 51 | 73 | Thick lumps | Firm brittle | Completely dissolved |
| 20100705-1.4 | 5 | 3.34 | 1154 | 224 | 63 | 88 | OK | Firm brittle | Somewhat thick at 90° C. dissolved |
| 20100705-1.5 | 10 | 3.23 | 1363 | 218 | >90 | >90 | OK | Firm brittle | Very thick at 90° C. not completely dissolved |
| 20100708-1.1 | 20 | 3.03 | 20.6 | 14.8 | >90 | >90 | OK | Very soft | Syneresis. Not dissolved |
| 20100708-1.2 | 15 | 3.11 | 347 | 152 | >90 | >90 | OK | Soft brittle | Some syneresis Not completely dissolved |

Table 14 compares gels made using varying concentrations of DA 24 LMA.

TABLE 14

Gels made with LMA—DA = 24. Effect of pectin concentration

| Sample | Pectin % | Glacial (ml) | pH | BS (g) | GS (g) | $T_G$ (° C.) | $T_M$ (° C.) | Disp. | Gel |
|---|---|---|---|---|---|---|---|---|---|
| 20101009-1.1 | 2 | 5 | 3.11 | 558 | 180 | 64 | 88 | OK Thin No lumps | Firm Wet Dissolved Brittle |
| 20101009-1.2 | 1 | 5 | 2.95 | — | — | — | — | OK | No gel |
| 20101020-1.3 | 2 | 0 | 3.26 | 868 | 138 | 59 | 86 | OK Thin No lumps | Firm Dry Dissolved Brittle |
| 20101110-1.1 | 1.5 | 5 | 3.04 | 101 | 46 | 56 | 83 | OK Thin No lumps | Wet Soft Dissolved |
| 20101110-1.2 | 1.5 | 0 | 3.19 | 453 | 98 | 60 | 86 | OK Thin No lumps | Firm Brittle Dissolved Dry |

Table 15 compares gels made with DA 18 LMA and varying volumes of glacial acetic acid.

TABLE 15

Gels made with LMA—DA = 18. Effect of glacial acetic acid

| Sample | Glacial (ml) | pH | BS (g) | GS (g) | $T_G$ (°C.) | $T_M$ (°C.) | Disp | Gel | Other comments |
|---|---|---|---|---|---|---|---|---|---|
| 20100708-1.3 | 0 | 3.3 | 233 | 56 | 57 | 83 | Some lumps | Firm Brittle | Dry Dissolved |
| 2.0100712-1.1 | 5 | 3.2 | 419 | 106 | 60 | 84 | OK | Firm Brittle | Dry Dissolved |
| 20100712-1.2 | 10 | 3.11 | 799 | 86 | >90 | >90 | OK | Firm Brittle | Dry Dissolved |
| 20100712-1.3 | 15 | 2.02 | 319 | 97 | >90 | >90 | OK | Firm Brittle | Dry Not Dissolved |

Table 16 compares gels made with varying concentrations of DA LMA.

TABLE 16

Gels made with LMA—DA = 18. Effect of pectin concentration

| Sample | Pectin % | Glacial (ml) | pH | BS (g) | GS (g) | $T_G$ (°C.) | $T_M$ (°C.) | Disp. | Gel |
|---|---|---|---|---|---|---|---|---|---|
| 20101009-1.4 | 2 | 5 | 3 | 299 | 93 | 60 | 86 | OK Thin No lumps | Wet Firm Brittle Dissolved |
| 20101110-1.3 | 1.5 | 5 | 2.96 | 82 | 33 | 54 | 79 | OK Thin No lumps | Wet Soft Brittle Dissolved |

Overall, the general trend observed with the amidated low ester pectin gel compositions is that solubility increases with decreasing degree of amidation. In these tests, a DA of about 31 was too high because in these compositions the pectin did not dissolve completely. Further, the solubility is further reduced when the pH is reduced with glacial acetic acid.

With a DA of about 24, up to 5 ml glacial acetic acid can be added to the gel compositions to a pH of about 3.34. However, the melting temperature of these compositions is high, and the resulting gel is brittle. As the pH is reduced with glacial acetic acid, the solubility decreases.

Without the addition of glacial acetic acid, the concentration of pectin must be at least 2% to avoid syneresis. With 5 ml glacial, the concentration of pectin must be 3% to avoid syneresis. With DA of about 18.5, 10 ml of glacial acetic acid can be added to the compositions to a pH about 3.11, and the pectin concentration must be about 3% to avoid syneresis. Thus, amidated low ester pectins provide for firm and brittle gels, the pH of which should not be reduced below about 2.95.

Publications cited herein and the materials for which they are cited are specifically incorporated by reference herein. Modifications and variations of the methods and compositions described herein will be obvious to those skilled in the art from the foregoing detailed description. Such modifications and variations are intended to come within the scope of the appended claims.

I claim:

1. An odor absorbing gel composition, comprising:
a low ester pectin in an amount from about 1.0 to about 3.5 percent by weight of the gel composition; and
acetic acid in an amount such that the gel composition has a pH from about 2.4 to about 3.5,
wherein the gel composition has a gel strength from about 5 grams to about 250 grams.

2. The composition of claim 1, wherein the low ester pectin is a conventional low ester pectin having a degree of esterification of less than about 55.

3. The composition of claim 2, wherein the conventional low ester pectin has a degree of esterification from about 15 to about 55.

4. The composition of claim 2, wherein the conventional low ester pectin has a degree of esterification from about 25 to about 45.

5. The composition of claim 2, wherein the conventional low ester pectin has a degree of esterification from about 30 to about 40.

6. The composition of claim 2, wherein the conventional low ester pectin is present in an amount from about 1.5 to about 3.5 percent by weight of the gel composition.

7. The composition of claim 1, wherein the low ester pectin is an amidated low ester pectin.

8. The composition of claim 7, wherein the amidated low ester pectin has a degree of amidation from about 15 to about 30.

9. The composition of claim 1, wherein the acetic acid comprises vinegar, glacial acetic acid, or a combination thereof.

10. The composition of claim 1, wherein the acetic acid comprises a combination of vinegar and glacial acetic acid having a weight ratio of glacial acetic acid to vinegar of less than about 0.35.

11. The composition of claim 1, wherein the acetic acid comprises a combination of vinegar and glacial acetic acid having a weight ratio of glacial acetic acid to vinegar less than about 0.15.

12. The composition of claim 2, wherein the gel composition has a pH from about 2.45 to about 3.25.

13. The composition of claim 7, wherein the gel composition has a pH from about 2.95 to about 3.45.

14. The composition of claim 1, further comprising calcium acetate in an amount from about 0.0160 to about 0.0220 percent by weight of the gel composition.

15. The composition of claim 2, wherein the gel composition has a gel strength from about 5 grams to about 40 grams.

16. The composition of claim 7, wherein the gel composition has a gel strength from about 30 grams to about 230 grams.

17. The composition of claim 2, further comprising calcium acetate in an amount from about 0.0160 to about 0.0220 percent by weight of the gel composition,
wherein the conventional low ester pectin has a degree of esterification from about 30 to about 40 and is present in an amount from about 1.5 to about 3.5 percent by weight of the gel composition.

18. The composition of claim 7, wherein:
the amidated low ester pectin has a degree of amidation from about 15 to about 30 and is present in an amount from about 2.0 to about 3.5 percent by weight of the gel composition, and
the acetic acid comprises vinegar.

19. The composition of claim 7, wherein:
the amidated low ester pectin has a degree of amidation from about 15 to about30 and is present in an amount from about 3.0 to about 3.5 percent by weight of the gel composition, and
the acetic acid comprises a combination of vinegar and glacial acetic acid having a weight ratio of glacial acetic acid to vinegar of from about 0.025 to about 0.05.

20. A method of making an odor absorbing gel composition, comprising:
dissolving a low ester pectin in an acetic acid solution to form an acidic pectin mixture;
heating the acidic pectin mixture to a temperature from about 80° C. to about 100° C.; and
cooling the mixture to room temperature to form a gel,
wherein the tow ester pectin is present in the gel composition in an amount from about 1.0 to about 3.5 percent by weight of the gel composition, the acetic acid is present in the gel composition in an amount such that the gel composition has a pH from about 2.4 to about 3.5, and the gel composition has a gel strength from about 5 grams to about 250 grams.

* * * * *

UNITED STATES PATENT AND TRADEMARK OFFICE
CERTIFICATE OF CORRECTION

PATENT NO. : 8,716,176 B2
APPLICATION NO. : 13/585493
DATED : May 6, 2014
INVENTOR(S) : Jens Eskil Trudsoe Page 1 of 1

It is certified that error appears in the above-identified patent and that said Letters Patent is hereby corrected as shown below:

In the Claims

At column 18, line 3, at "about30" add a space between the letter "t" and numeral "3".

Signed and Sealed this
Fifteenth Day of July, 2014

Michelle K. Lee
*Deputy Director of the United States Patent and Trademark Office*